United States Patent
Yamasaki et al.

(10) Patent No.: US 6,242,648 B1
(45) Date of Patent: Jun. 5, 2001

(54) PROCESS FOR PREPARING TRIARYLAMINE DIMER

(75) Inventors: Yasuhiro Yamasaki; Kazuyoshi Kuroda, both of Neyagawa (JP)

(73) Assignee: Orient Chemical Industries, Ltd., Osaka (JP)

( * ) Notice: Subject to any disclaimer, the term of this patent is extended or adjusted under 35 U.S.C. 154(b) by 0 days.

(21) Appl. No.: 09/478,817

(22) Filed: Jan. 7, 2000

(30) Foreign Application Priority Data

Aug. 1, 1999 (JP) ................................... 11-002845

(51) Int. Cl.$^7$ ................................................ C07C 209/00
(52) U.S. Cl. .............................................................. 564/405
(58) Field of Search ............................................. 564/405

(56) References Cited

U.S. PATENT DOCUMENTS

| | | |
|---|---|---|
| 3,484,467 | 12/1969 | Susi et al. . |
| 5,605,732 | 2/1997 | Mihara et al. . |
| 5,853,930 | 12/1998 | Kondoh . |

FOREIGN PATENT DOCUMENTS

| | | |
|---|---|---|
| 0802173A1 | 10/1997 | (EP) . |
| 6321872 | 11/1994 | (JP) . |
| 179319 | 7/1997 | (JP) . |
| 1017531 | 1/1998 | (JP) . |

OTHER PUBLICATIONS

Gauthier et al., Synthesis, pp. 383–394 (1987).
Sukuta et al., J. Org. Chem., vol. 54, No. 6, pp. 1476–1479 (1989).

*Primary Examiner*—Samuel Barts
(74) *Attorney, Agent, or Firm*—Birch, Stewart. Kolasch & Birch, LLP (57) ABSTRACT

The present invention intends to provide a simple process for preparing triarylamine dimer without using any expensive chemicals, the process being able to achieve high reaction yield and being advantageous to be carried out on an industrial scale. The present invention provides a process for preparing triarylamine dimer (I) using the Ullmann reaction represented by the scheme:

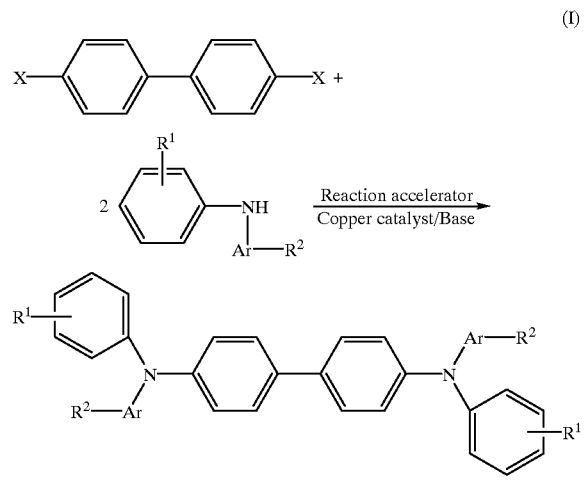

wherein X represents a halogen atom, $R^1$ and $R^2$ represent independently a hydrogen atom, an alkyl group, an alkoxy group or a halogen atom, Ar represents a phenylene group, or a naphthylene group, characterized in that the reaction accelerator is polyethylene glycol or di- or monoalkyl ether of polyethylene glycol.

6 Claims, 4 Drawing Sheets

PROCESS FOR PREPARING TRIARYLAMINE DIMER

BACKGROUND OF THE INVENTION

The present invention relates to a process for preparing triphenylamine dimer, or triarylamine dimer useful as a material for electrophotography, a material for organic electroluminescence (EL), and the like. Particularly, the present invention concerns an industrially advantageous process for preparing triarylamine dimer, or triarylamine dimer utilizing the Ullmann reaction.

An electrophotographic photoreceptor is a member which forms a latent image of charges in a surface area when a beam light corresponding to an image has been irradiated. An organic electrophotographic photoreceptor has an organic photoconductive material on a conductive support. The organic photoconductive material is formed by binding photoconductive compounds with an organic resin.

In general, an organic photoreceptor has a charge-generating layer containing a charge-generating material which generates a charge by light irradiation, such as phthalocyanines, and a charge-transporting layer containing a charge-transporting material which transports a charge to the surface of the photoreceptor.

As a charge-transporting material used for an organic electrophotographic photoreceptor have been known triarylamine compounds, oxazole derivatives, oxadiazole derivatives, pyrazoline derivatives, hydrazone derivatives, hydrazine derivatives, triazine derivatives, quinazoline derivatives, styryl compounds, styryltriphenylamine compounds, butadiene compounds, carbazole compounds, etc. Benzofuran compounds recently reported (Japanese Patent Kokai Publication No. 179319/1997) may also be exemplified.

Triarylamine dimer has been used for an electrophotographic material, an organic electroluminescence (EL) material and the like. Particularly, it has been widely applied as a charge-transporting material (CTM) of organic electrophotographic photoreceptors used in copying machines, printers and the like or as a hole-transporting material (HTM) used in EL devices.

Hitherto, aromatic tertiary amine compounds having two aromatic tertiary amine and containing a biphenylene group in the molecule, such as triarylamine dimer, have been prepared by using benzidine as a starting material. Benzidine, however, is a carcinogenic compound, therefore, such a process is not put into practice today (See U.S. Pat. No. 3,484,467 and Japanese Patent Kokai Publication No. 321872/1994).

An example of a process for preparing triarylamine dimer without using benzidine as a starting material is disclosed in Japanese Patent Kokai Publication No. 17531/1998. Examples following Example 13 of that publication disclose a process for preparing triphenylamine dimer in which iodinated triphenylamine and hydroxyboronated triphenylamine are coupled in the presence of a palladium catalyst. This process, however, has drawbacks of that the expensive palladium catalyst is required, and separation and recovery of the catalyst after reaction is required.

On the other hand, a process utilizing the Ullmann reaction has been reported as a general process for synthesizing an aromatic tertiary amine compound. For instance, Synthesis, pp. 383 to 384 (1987) discloses a process for preparing triphenylamine using the reaction of the following scheme:

This reaction uses metallic copper as a catalyst, potassium carbonate as base, crown ether (18-crown-6-ether) as a reaction accelerator and o-dichlorobenzene as a reaction solvent.

EP0802173A1 discloses a process for synthesizing aromatic tertiary amines in which an aromatic halogenated compound and aromatic secondary amine are reacted in the presence of palladium tert-phosphine (for example, P(o-tolyl)$_3$Pd) as a catalyst and tert-BuONa as base.

Alternatively, J. Org. Chem., Vol. 54, No. 6, 1989, pp. 1476 to 1479 discloses a process for synthesizing aromatic tertiary amines in which an aromatic halogenated compound and aromatic secondary amine are reacted in the presence of metallic copper as a catalyst, alkali metal hydroxide as base and polyethylene glycol (PEG) or polyethylene glycol dialkyl ether (PEGDM) as a reaction accelerator or a reaction solvent.

Although in the prior art on the Ullmann reaction, a variety of aromatic tertiary amines have been synthesized, no publication discloses an example of synthesizing triarylamine dimer.

Moreover, in the process using crown ether as a reaction accelerator, the crown ether is expensive and the process requires too much cost to be put into practice on an industrial scale. The process using palladium tert-phosphine has drawbacks of that an expensive palladium catalyst is required, and separation and recovery of a catalyst after reaction is required. The process using PEG or PEGDM as a reaction accelerator and a reaction solvent has a problem of that the yield of the product, which is no less than 40%, is too low to be carried out on an industrial scale.

SUMMARY OF THE INVENTION

The present invention has solved the above-mentioned problems of the conventional processes, and the object thereof is to provide a simple process for preparing triarylamine dimer without using any expensive reagent, the process being able to achieve high reaction yield and being advantageous to be carried out on an industrial scale.

The present invention provides a process for preparing triarylamine dimer (I) using the Ullmann reaction represented by the scheme:

(I)

wherein X represents a halogen atom, $R^1$ and $R^2$ represent independently a hydrogen atom, an alkyl group, an alkoxy group or a halogen atom, Ar represents a phenylene group, or a naphthylene group (preferably an a-naphthylene group), characterized in that the reaction accelerator is polyethylene glycol or di- or monoalkyl ether of polyethylene glycol.

The terms alkyl and alkoxy, when used alone or in combination with other terms throughout the application, refers to linear or branched alkyl and alkoxy, preferably lower alkyl and alkoxy, most preferably $C_1$ to $C_4$ alkyl such as methyl, ethyl, propyl, isopropyl, butyl, and isobutyl, and $C_1$ to $C_4$ alkoxy such as methoxy, ethoxy, propoxy, isopropoxy, butoxy, and isobutoxy.

The process of the present invention preferably have the step of undergoing the N-arylation reaction of 4,4'-dihalobiphenyl and diarylamine in the presence of base, a copper catalyst, and polyethylene glycol or di- or monoalkyl ether of polyethylene glycol as a reaction accelerator.

DETAILED DESCRIPTION OF THE INVENTION

The process for preparing triarylamine dimer (I) utilizing the Ullmann reaction is characterized in that polyethylene glycol (in this specification, referred to as PEG) or di- or monoalkyl ether of polyethylene glycol (in this specification, referred to as PEGM) as a reaction accelerator (a phase transfer catalyst). The process will be explained in detail below.

First, 4,4'-dihalobiphenyl represented by the following formula (3) is prepared:

(3)

wherein X has the same meaning as previously defined.

Preferred are 4,4'-dibromobiphenyl and 4,4'-diiodobiphenyl from the viewpoint of reactivity. Particularly preferred is 4,4'-diiodobiphenyl. These may be synthesized. Alternatively, commercially available ones may be employed.

Subsequently, diarylamine is prepared. As the diarylamine, the aromatic secondary amine represented by the following formula (1) can be used:

(1)

wherein $R^1$, $R^2$, and Ar have the same meaning as previously defined. Preferred are the aromatic secondary amines represented by the following formulae (2-1) and (2-2):

(2-1)

(2-2)

These may be synthesized. Alternatively, commercially available ones may be used.

In the next step, the 4,4'-dihalobiphenyl and the diarylamine are subjected to the N-arylation reaction in the presence of base, a copper catalyst and a reaction accelerator.

Examples of the base include alkali metal hydroxides such as sodium hydroxide and potassium hydroxide; alkali metal carbonates such as potassium carbonate and sodium carbonate; trialkylamines such as triethylamine and triisopropylamine; and metal alkoxides such as tert-BuONa and tert-BuOK. From the viewpoint of production cost (yield and cost of raw materials), potassium carbonate is particularly preferred. A metallic copper (Cu(0)) is used as the copper catalyst. The amounts of the base and the copper catalyst may be the same as those set in the conventional Ullmann reaction.

As the reaction accelerator or the phase transfer catalyst is used PEG or PEGM. Preferably, PEG or PEGM selected from the group consisting of the compounds represented by the following formulae (i) to (iii) is used.

PEG represented by the formula:

$$HO(CH_2CH_2O)_a\text{—}H \qquad (i)$$

wherein a represents an integer of not less than 2. For example, diethylene glycol, triethylene glycol, tetraethylene glycol, which are represented by the formula (i) wherein a is from 2 to 4, polyethylene glycol and mixtures thereof may be used. Specifically, PEG-6000 (a trade name) manufactured by Wako Junyaku K.K. may be employed.

PEGM represented by the formula:

$$R^3O(CH_2CH_2O)_b\text{—}R^4 \qquad (ii)$$

wherein $R^3$ and $R^4$ represent the same or different alkyl groups having 1 to 4 carbon atoms and b represents an integer of not less than 2. For example, diethylene glycol dimethyl ether (diglyme), triethylene glycol dimethyl ether (triglyme), tetraethylene glycol dimethyl ether (tetraglyme), which are represented by the formula (ii) wherein b is from 2 to 4, polyglyme, mixtures thereof, diethylene glycol diethyl ether and diethylene glycol methyl ethyl ether may be used. Specifically, PMP400 (a trade name) manufactured by Toho Kagaku K.K. may be employed.

PEGM represented by the formula:

$$R^3O(CH_2CH_2O)_c\text{—}H \qquad (iii)$$

wherein $R^3$ represents an alkyl group having 1 to 4 carbon atoms and c represents an integer of not less than 2. For example, diethylene glycol monomethyl ether, diethylene glycol monoethyl ether, diethylene glycol monoisopropyl ether, diethylene glycol monobutyl ether, triethylene glycol monomethyl ether, tetraethylene glycol monomethyl ether, which are represented by the formula (iii) wherein c is from 2 to 4, and mixtures of polyethylene glycol monoethers may be employed.

The amount of the reaction accelerator used is from 1/10 to 10 times, preferably from 1/10 to 1/5 times per gram of the 4,4'-dihalobiphenyl. The N-arylation reaction may be conducted using, as a reaction solvent, PEG or PEGM which serves as the reaction accelerator, or may be performed using other suitable reaction solvent. The reaction is usually carried out by charging a reaction solvent, 4,4'-dihalobiphenyl, diarylamine, base (preferably sodium carbonate), a copper catalyst and a reaction accelerator into an appropriate vessel, followed by stirring for 5 to 40 hours with maintaining the temperature at 100 to 250° C.

As the reaction solvent, (high boiling) aromatic solvents such as xylene, o-dichlorobenzene, quinoline, α-or β-chloronaphthalene, α-methylnaphthalene and nitrobenzene; amide solvents such as N-methylformamide, N,N'-dimethylformamide (DMF), N-methylacetamide, N-methylpyrrolidone, N-methyl-2-piperidone; and the like can be used. Preferred are high boiling aromatic solvents such as o-dichlorobenzene and nitrobenzene.

The process of the reaction can be traced by a conventional method such as chromatography. After the completion of the reaction, the solvent is removed by distillation, and the product is isolated and purified by a conventional method such as the chromatography method. The structure of the product can be identified by elemental analysis, MS (FD-MS) analysis, IR analysis, $^1$H-NMR and $^{13}$C-NMR.

An embodiment of the present invention is described below.

To 4,4'-dihalobiphenyl (for example, 1.0 g of 4,4'-diiodobiphenyl) is added a reaction solvent (for example, 20 ml of o-dichlorobenzene), and additionally added diphenylamine (for example, 1.08 g of m-methyldiphenylamine), base (for example, 2.73 g of potassium carbonate), a copper catalyst (for example, 0.635 g of copper powder) and a reaction accelerator PEG (for example, 0.104 g of PEG-6000 (a trade name)). The mixture is refluxed under stirring until the reaction is completed (for about 15 to 24 hours). After the completion of the reaction, the resulting mixture is hot-filtrated to yield a product, which is then washed with a solvent such as dichloromethane. The solvent is removed by distillation under reduced pressure. The residue is purified by silica gel chromatography to afford triphenylamine dimer (for example, N,N'-diphenyl-N,N'-ditolyl-4,4'-diaminobiphenyl [TPD]). 4,4'-dihalobiphenyl (25.1 g of 4,4'-diiodobiphenyl), a reaction accelerator PEG (for example, 2.14 g of PEG-6000 (a trade name)), base (for example, 17.1 g of potassium carbonate), a copper catalyst (for example, 15.7 g of copper powder) are added to diarylamine (for example, 32.4 g of N-phenyl-1-naphthylamine). The mixture is heated to 200° C., and stirred at this temperature until the reaction is completed (for about 15 to 24 hours). After the completion of the reaction, water and DMF are added, and the resulting mixture is dispersed, filtrated, and washed with water. The resulting crystal is purified by silica gel chromatography to afford triarylamine dimer (for example, N,N'-di(1-naphthyl)-N,N'-diphehyl-4,4'-diaminobiphenyl [α-NPD]).

By performing the reaction by the process of the present invention using the preceding reaction reagent (chemicals and a solvent), triarylamine dimer (e.g., TPD or α-NPD) can be provided in high yield.

The TPD and the aromatic tertiary amine derivative prepared by the process of the present invention are useful as a charge-transporting materials of the organic electrophotographic photoreceptors, and hole-transporting materials used for the organic film electroluminescence (EL) devices utilizing the organic EL phenomena. Examples of applications to EL devices include an electroluminescence apparatus having an organic electroluminescence medium disclosed in Applied Physics Letter, Vol. 57, No. 6, 531 (1990) and Japanese Patent Kokai Publication No. 234681/1993, and a phenazasiline compound and the organic film EL device using the compound disclosed in Japanese Patent Kokai Publication No. 218884/1998.

Particularly, the triarylamine dimer such as TPD and α-NPD prepared by the process of the present invention has high purity and stable photosensitive characteristic. Accordingly, a charge-transporting material for organic electrophotographic photoreceptors containing the TPD prepared by the process of the present invention is useful. In addition, the organic electrophotographic photoreceptor containing this charge-transporting material is also useful Examples of applications of the triarylamine dimer prepare by the process of the present invention to the organic photoreceptors are described below.

The triarylamine dimer such as TPD and α-NPD is useful as a charge-transporting material (CTM) for organic electrophotographic photoreceptors which has been widely applied to copying machines and the like which utilizes electrophotographic technology. In addition, the triarylamine dimer of the present invention can provide a photoreceptor having good charging property, medium or high photoresponse and high durability (durability in photoresponse and durability in potential) when used in combination with phthalocyanine charge-generating materials (CGM) such as titanyl phthalocyanine, $\mu$-oxo-aluminum phthalocyanine dimer and $\mu$-oxo-gallium phthalocyanine dimer.

Organic electrophotographic photoreceptors containing at least one organic photoconductive pigment like phthalocyanine and a resin may be either of laminated type in which a photosensitive layer is separated into a charge-generating layer (CGL) and a charge-transporting layer (CTL) or of single-layer type. In order to make use of electric characteristic and photosensitive characteristic of a specific crystalline modification of the phthalocyanine charge-generating agent efficiently, such ar agent is preferably applied to a function-separating photoreceptor having two-layer structure in which charges generated have little possibility to be captured, and they are transported efficiently to the surface of the photoreceptor.

Such a function-separating photoreceptor is formed, for example, by laminating a film-like charge-generating and film-like charge-transporting layers on a conductive support. As a substrate of the conductive support, metal such as aluminum and nickel, and metal-deposited films may be used. Such a substrate is prepared in the form of dram, sheet or belt.

When the triarylamine dimer is applied to organic electrophotographic photoreceptors, a film-like charge-generating layer containing a photoconductive phthalocyanine pigment as a charge-generating material (CG material) is formed first on a conductive support. In the formation of the charge-generating layer, the film may be formed by depositing the phthalocyanine pigment on a conductive support, however, the film is generally formed by applying a coating liquid, which is prepared by dispersing a charge-generating material in a solution containing a binding resin and a solvent, onto the support.

As a method for dispersing the phthalocyanine pigment (CGM), conventional dispersing methods using a ball mill, sand mill, a paint shaker or the like may be adopted.

Means for forming the charge-generating layer has no particular limitations. For example, a bar coater, a dip coater, a spin coater, a roller coater and the like can be employed as appropriate. Drying can be conducted at temperatures of from 30 to 200° C. for a period of time of from 5 minutes to 2 hours, with still standing or under ventilation.

The solvent for the coating liquid has no particular limitations so long as it can disperse the phthalocyanine pigment uniformly without dissolving it and can dissolve the binding resin used as demanded. Examples of such a solvent include alcohol solvents such as methanol, ethanol, isopropanol and butanol; aromatic solvents such as toluene, xylene and tetralin; halogen-containing solvents such as dichloromethane, chloroform, trichloroethylene and carbon tetrachloride; ester solvents such as ethyl acetate and propyl acetate; ether solvents such as ethylene glycol monoethyl ether, dioxane and tetrahydrofuran; dimethylformamide and dimethyl sulfoxide.

The binding resin can be selected from a wide variety of insulating resins. Preferred are, for example, condensed resins such as polycarbonate, polyester, polyamide and polyallylate; addition polymerization products such as polystyrene, polyacrylate, styrene-acryl copolymer, polyacrylamide, polymethacrylate, polyvinylbutyral, polyvinyl alcohol, polyacrylnitrile, polyacryl-butadiene copolymer, polyvinyl chloride and vinyl chloride-vinyl acetate copolymer; organic photoconductive resins such as poly-N-vinylcarbazole and polyvinylanthracene; polysulfones, polyether sulfones, silicone resins, epoxy resins and urethane resins. These may be mixed as appropriate to be used.

The amount of the above-mentioned binding resin is from 0.1 to 3 ratio by weight based on the charge-generating material. The amount of more than 3 ratio by weight results in a low concentration of the charge-generating material in the charge-generating layer and in a poor photosensitivity. The thickness of the charge-generating layer is from 0.05 to 5.0 $\mu$m, usually not more than 10 $\mu$m.

Subsequently, a film-like charge-transporting layer containing a charge-transporting material is formed on the charge-generating layer. For forming the film, the method similar to that employed for forming the charge-generating layer may be employed. Namely, the charge-transporting material may be dissolved in a solvent, if necessary, together with a binding resin, applied uniformly onto the charge-generating layer, and then dried.

As the charge-transporting material (CTM), the triarylamine dimer (e.g., TPD or $\alpha$-NPD) prepared by the process of the present invention is used.

A binding resin and a solvent for forming the charge-transporting layer may be those used for the charge-generating layer.

The amount of the binding resin used is from 0.1 to 5 ratio by weight based on the charge-transporting material. The amount of more than 5 ratio by weight results in low concentration of the charge-transporting material in the charge-transporting layer and in poor photosensitivity (photoresponse). The thickness of the charge-transporting layer is from 5 to 50 $\mu$m, usually not more than 100 $\mu$m.

Furthermore, the charge-generating layer, the charge-transporting layer or a surface-protecting layer may contain a variety of conventional additives such as sensitizers; anti-degradation agents, e.g., amine-form or phenol-form antioxidants and ultraviolet absorbers of benzophenone type; etc.

The following examples further illustrate the present invention, however, these are not to be construed as limiting the present invention to their details.

EXAMPLE 1

Synthesis of N,N'-diphenyl-N,N'-ditolyl-4,4'-diaminobiphenyl

Figure 1:
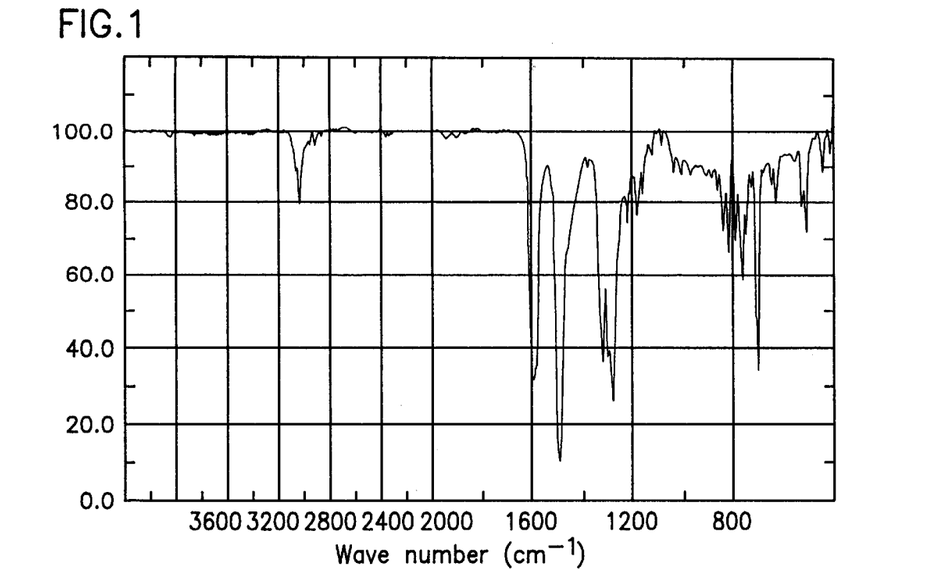
FIG. 1 is an IR spectrum of the triphenylamine dimer TPD) obtained in Example 1.
Figure 2:
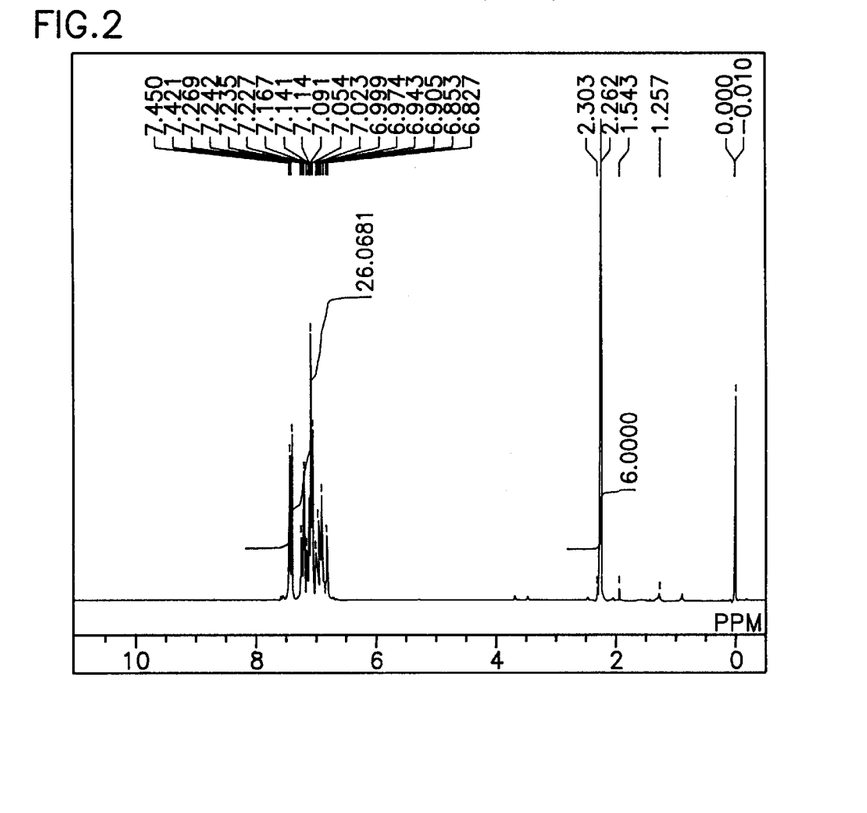
FIG. 2 is a $^1$H-NMR spectrum of the triphenylamine dimer (TPD) obtained in Example 1.
Figure 3:
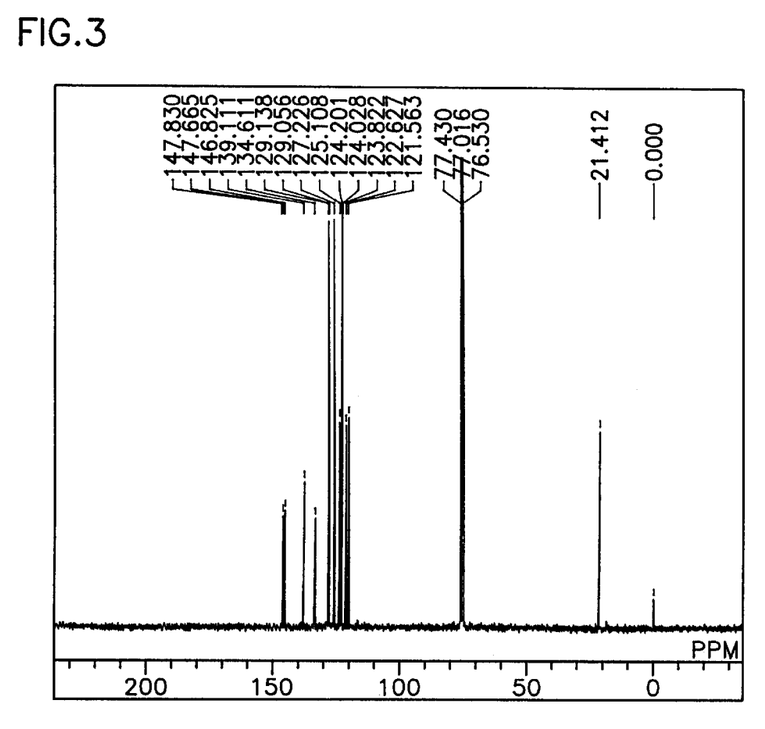
FIG. 3 is a $^{13}$C-NMR spectrum of the triphenylamine dimer (TPD) obtained in Example 1.
Figure 4:
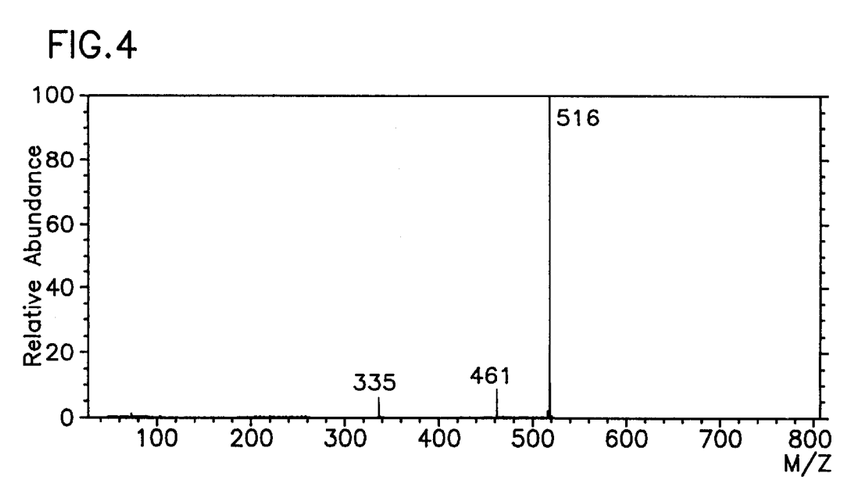
FIG. 4 is an FD-MS spectrum of the triphenylamine dimer (TPD) obtained in Example 1.

Into a glass four-necked flask equipped with a stirring device and a coiled condenser were added 1.0 g (2.46 mmol) of 4,4'-diiodobiphenyl and 20 ml of o-dichlorobenzene, and additionally, 1.08 g (5.90 mmol) of m-methyldiphenylamine, 0.104 g of polyethylene glycol (PEG-6000 (a trade name) manufactured by Wako Junyaku K.K.) as a reaction accelerator, 2.73 g (0.0198 mol) of potassium carbonate and 0.635 g (9.87 mmol) of copper (powder) were added. The mixture was refluxed under stirring. The reaction was traced by high-performance liquid chromatography. Reflux was continued under stirring until the peaks of raw materials and intermediates were disappeared (for 22 hours). After hot-filtration, the product was washed with dichloromethane until the color of the filtrate became pale and the solvent was removed by distillation under reduced pressure. The residue was purified by silica gel chromatography to afford 1.01 g (yield: 78.7%) of N,N'-diphenyl-N,N'-ditolyl-4,4'-diaminobiphenyl represented by the following formula:

The elemental analysis is shown in Table 1. The IR analysis is shown in FIG. 1. The $^1$H-NMR spectrum, $^{13}$C-NMR spectrum and FD-MS spectrum are shown in FIGS. 2, 3 and 4, respectively.

TABLE 1

|  | C | H | N |
|---|---|---|---|
| Calculated % | 88.34 | 6.24 | 5.42 |
| Found % | 87.87 | 6.30 | 5.25 |

The measurement of FD-MS (mass spectrometric analysis by a field desorption ionization method) was conducted under the following conditions:

(1) Measuring method

TABLE 2

| Measuring device | MS: JVS-DX303HF (manufactured by JEOL K.K.) |
|---|---|
| Measuring conditions | FD method, using a carbon emitter |
| | Dissolution: 500, 35–2500 M/Z |
| | Accelerating voltage: 2.5 kV |
| | Ion multiplyer: 1.2–1.6 kV |
| | Emitter current: 0–40 mA |
| | Cathode voltage: 5.0 kV |
| | Sample: DMF solution |

(2) Result of Measurement: FIG. 4

In the figure, the horizontal axis indicates M/Z [mass/charge], the vertical axis indicates relative abundance. An ion peak of N,N'-diphenyl-N,N'-ditolyl-4,4'-diaminobiphenyl [$C_{38}H_{32}N_2$] is observed at M/Z=516 (100) [M+H]$^+$.

EXAMPLE 2

Synthesis of N,N'-diphenyl-N,N'-ditolyl-4,4'-diaminobiphenyl

To 10.8 g (59.0 mmol) of m-methyldiphenylamine and 10.0 g (24.6 mmol) of 4,4'-diiodobiphenyl were added 1.04 of polyethylene glycol (PEG-6000 (a trade name) manufactured by Wako Junyaku K.K.), 27.3 g (0.198 mol) of potassium carbonate and 6.35 g (98.7 mmol) of copper (powder), and heated to 205° C. The reaction was traced by high-performance liquid chromatography. Heating was continued until the peaks of raw materials and intermediates were disappeared (for 9 hours). To the mixture was added 270 ml of a 25% aqueous ammonia and heated at 80 to 90° C. for 15 minutes. The resulting mixture was hot-filtered and the residue was washed with a small amount of 25% aqueous ammonia and tap water. The resulting crystal was purified by silica gel chromatography to afford 9.43 g (yield: 73.6%) of N,N'-diphenyl-N,N'-ditolyl-4,4'-diaminobiphenyl.

The elemental analysis, IR analysis, $^1$H-NMR spectrum, $^{13}$C-NMR spectrum and FD-MS spectrum were the same as those of Example 1.

EXAMPLE 3

Synthesis of N,N'-diphenyl-N,N'-ditolyl-4,4'-diaminobiphenyl

To 1.0 g (2.46 mmol) of 4,4'-diiodobiphenyl was added 20 ml of o-dichlorobenzene, and additionally, 1.08 g (5.90 mmol) of m-methyldiphenylamine, 0.104 g of polyethylene glycol dimethyl ether (PMP-400 (a trade name) manufactured by Toho Kagaku K.K.), 2.73 g (0.0198 mol) of potassium carbonate and 0.635 g (9.87 mmol) of copper (powder) were added. The mixture was refluxed under stirring. The reaction was traced by high-performance liquid chromatography. Reflux was continued under stirring until the peaks of raw materials and intermediates were disappeared (for 30 hours). After hot-filtration, the product was washed with dichloromethane until the color of the filtrate became pale and the solvent was removed by distillation under reduced pressure. The residue was purified by silica gel chromatography to afford 0.865 g (yield: 67.8%) of N,N'-diphenyl-N,N'-ditolyl-4,4'-diaminobiphenyl.

The elemental analysis, IR analysis, $^1$H-NMR spectrum, $^{13}$C-NMR spectrum and FD-MS spectrum were the same as those 15 of Example 1.

EXAMPLE 4

Synthesis of N,N'-diphenyl-N,N'-ditolyl-4,4-diaminobiphenyl

To 1.0 g (2.46 mmol) of 4,4'-diiodobiphenyl was added 20 ml of o-dichlorobenzene, and additionally, 1.08 g (5.90 mmol) of m-methyldiphenylamine, 0.104 g of polyethylene glycol (PEG-6000 (a trade name) manufactured by Wako Junyaku K.K.), 1.11 g (0.0198 mol) of potassium hydroxide and 0.635 g (9.87 mmol) of copper (powder) were added. The mixture was refluxed under stirring. The reaction was traced by high-performance liquid chromatography. Reflux was continued under stirring until the peaks of raw materials and intermediates were disappeared (for 66 hours). After hot-filtration, the product was washed with dichloromethane until the color of the filtrate became pale and the solvent was removed by distillation under reduced pressure. The residue was purified by silica gel chromatography to afford 0.416 g (yield: 32.5%) of N,N'-diphenyl-N,N'-ditolyl-4,4'-diaminobiphenyl.

The elemental analysis, IR analysis, $^1$H-NMR spectrum, $^{13}$C-NMR spectrum and FD-MS spectrum were the same as those of Example 1.

EXAMPLE 5

Synthesis of N,N'-di(1-naphthyl)-N,N'-diphenyl-4,4'-diaminobiphenyl (α-NPD)

Figure 5:
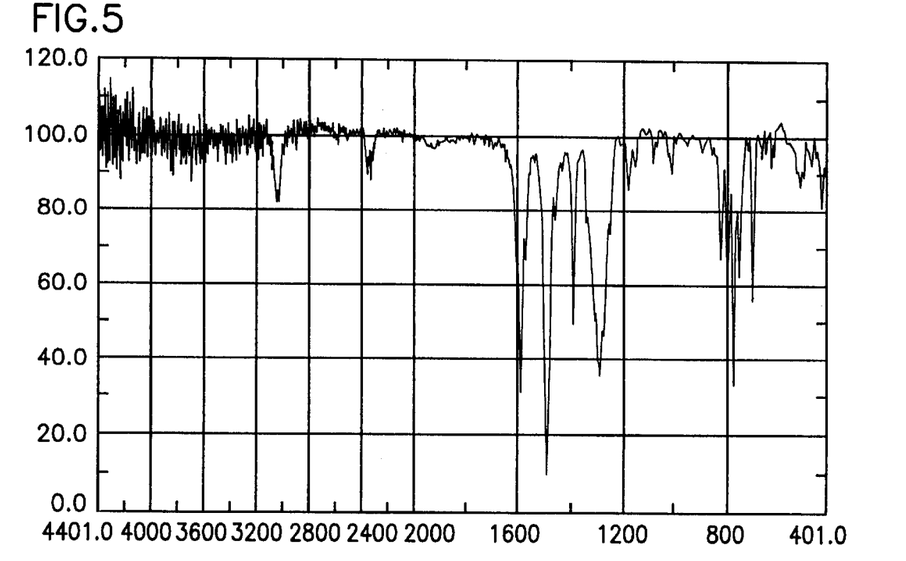
FIG. 5 is an IR spectrum of the triarylamine dimer (α-NPD) obtained in Example 5.
Figure 6:
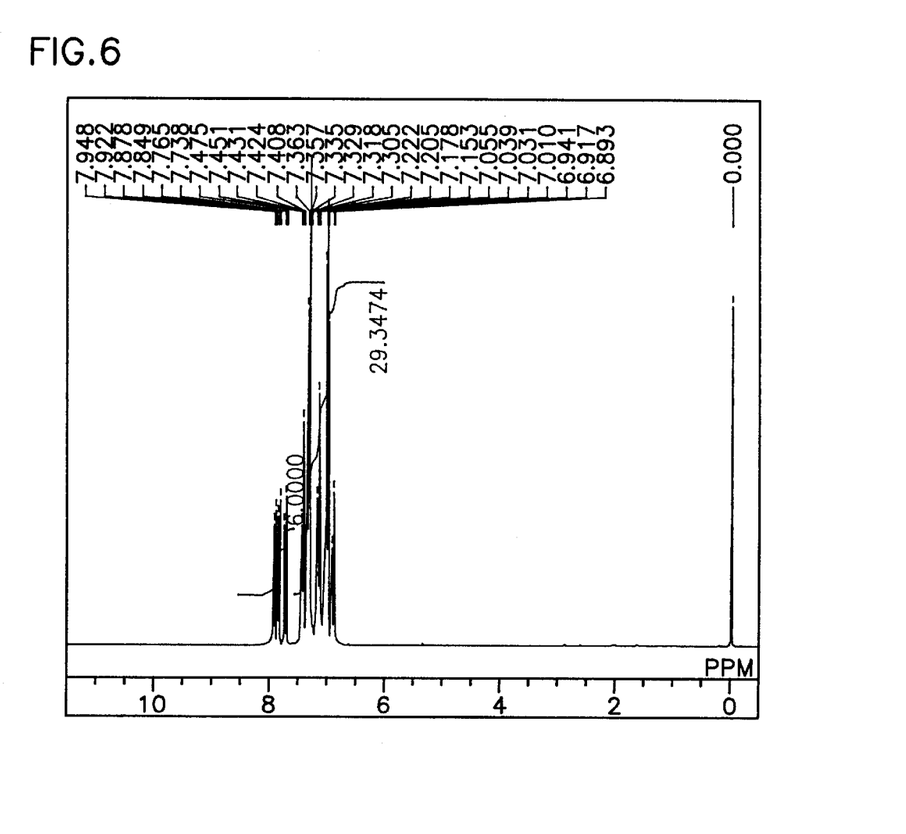
FIG. 6 is a $^1$H-NMR spectrum of the triarylamine dimer (α-NPD) obtained in Example 5.
Figure 7:
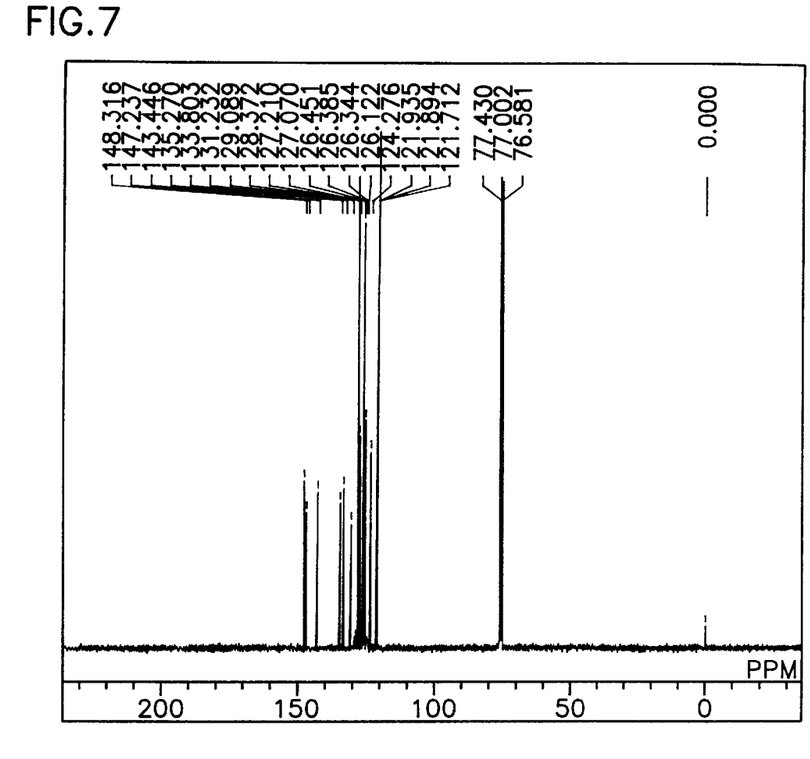
FIG. 7 is a $^{13}$C-NMR spectrum of the triarylamine dimer (α-NPD) obtained in Example 5.
Figure 8:
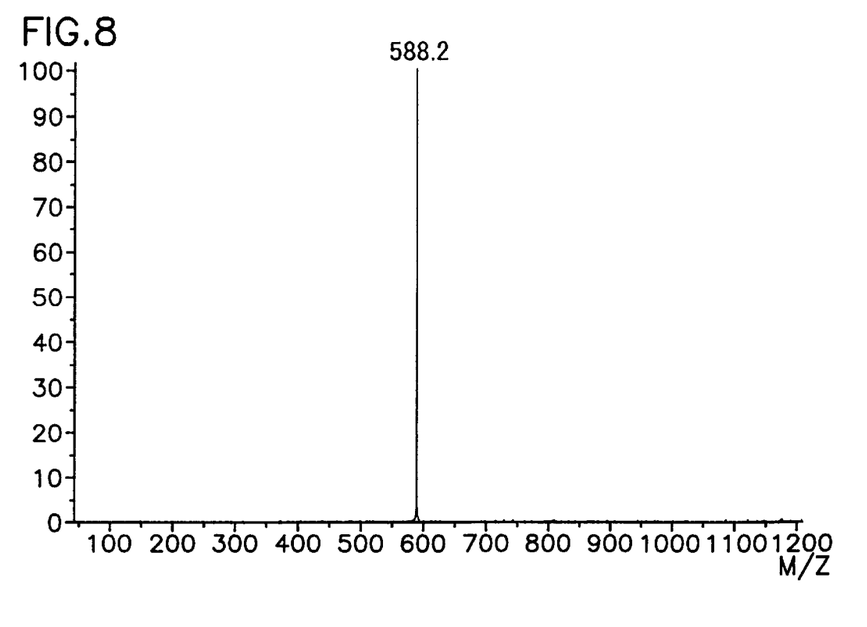
FIG. 8 is an FD-MS spectrum of the triarylamine dimer (α-NPD) obtained in Example 5.

To 32.4 g (148 mmol) of N-phenyl-1-naphthylamine were added 25.1 g (61.5 mmol) of 4,4'-diiodobiphenyl, 2.14 g of polyethylene glycol (PEG-6000 (a trade name) manufactured by Wako Junyaku K.K.), 17.1 g (0.124 mol) of potassium carbonate and 15.7 g (247 mmol) of copper (powder) were added, and heated to 200° C. The reaction was traced by high-performance liquid chromatography. Heating was continued under stirring until the peaks of raw materials and intermediates were disappeared (for 12 hours). After the completion of the reaction, water and DMF are added, and the resulting mixture is dispersed, filtrated, and washed with water. The resulting crystal is purified by silica gel chromatography to afford 20.2 g (yield: 55.9%) of N,N'-di(1-naphthyl)-N,N'-diphenyl-4,4'-diaminobiphenyl represented by the formula:

The IR analysis is shown in FIG. 5. The $^1$H-NMR spectrum, $^{13}$C-NMR spectrum and FD-MS spectrum are shown in FIGS. 6, 7 and 8, respectively.

Comparative Example 1

To 1.01 g (2.47 mmol) of 4,4'-diiodobiphenyl was added 20 ml of o-dichlorobenzene, and additionally, 0.95 g (5.20 mmol) of m-methyldiphenylamine, 0.141 g (0.493 mmol) of 18-crown-6-ether, 2.73 g (0.0197 mol) of potassium carbonate and 0.625 g (9.85 mmol) of copper (powder) were added. The mixture was refluxed under stirring. The reaction was traced by high-performance liquid chromatography. Reflux was continued under stirring until the peaks of raw materials and intermediates were disappeared (for 19 hours). After hot-filtration, the product was washed with 10 ml of chloroform and the solvent was removed by distillation under reduced pressure. The residue was purified by silica gel chromatography to afford 0.871 g (yield: 32.8%) of N,N'-diphenyl-N,N'-ditolyl-4,4'-diaminobiphenyl.

Comparative Example 2

In 44.0 ml of xylene was dissolved 1.00 g (2.46 mmol) of 4,4'-diiodobiphenyl, and additionally 0.947 g (5.17 mol) of m-methyldiphenylamine, 22.5 mg (0.0246 mmol) of dibenzylideneacetone dipalladium salt, 30.0 mg (0.098 mmol) of tri-o-tolylphosphine and 1.32 g (0.0314 mol) of sodium tert-butoxide. The mixture was refluxed under stirring. The reaction was traced by high-performance liquid chromatography. Reflux was continued under stirring until the peaks of raw materials and intermediates were disappeared (for 10 hours). After filtration using Celite, the product was washed with 10 ml of dichloromethane until the filtrate became pale and the solvent was removed by distillation under reduced pressure. The residue was purified by silica gel chromatography to afford 0.622 g (yield: 48.9%) of N,N'-diphenyl-N,N'-ditolyl-4,4'-diaminobiphenyl.

EXAMPLE 6

Into a wide mouthed bottle (140 ml) were placed 0.20 g of Y-form titanyl phthalocyanine (Ti(=O) Pc) described in Japanese Patent Kokoku Publication No. 35064/1991, 0.20 g of polyvinylbutyral resin [ELEX BH-3 manufactured by Sekisui Kagaku K.K.] and 59.6 g of cyclohexanone together with 50 g of 3 mmφ glass beads. After stirring by a paint shaker for 1 hour, the mixture was applied to an aluminum board, which had been washed carefully with acetone, using a bar coater to form a charge-generating layer (CGL) so that the thickness of film becomes 0.5 μm. Subsequently, onto the resulting charge-generating layer, a homogeneous solution, which had been prepared by mixing 4.5 g of the triarylamine dimer (TPD) prepared in Example 1, 4.5 g of a polycarbonate resin [PANLITE L-1250 manufactured by Teijin K.K.] and 51.0 g of dichloromethane and conducting ultrasonic dispersion, was applied with a bar coater to form a charge-transporting layer (CTL) so that the thickness of film becomes 60 μm. This was dried overnight to provide a photoreceptor (piece) for test.

EXAMPLE 7

A photoreceptor (piece) for test was prepared in the same manner as Example 6 except for replacing the Y-form titanyl phthalocyanine used in Example 6 with II-form μ-oxo-aluminum phthalocyanine dimer (μ-oxo-Al Pc dimer) described in Japanese Patent Kokai Publication No. 217020/1997.

EXAMPLE 8

A photoreceptor (piece) for test was prepared in the same manner as Example 6 except for replacing the Y-form titanyl phthalocyanine used in Example 6 with G-form μ-o-gallium phthalocyanine dimer (μ-oxo-Ga Pc dimer) described in Japanese Patent Kokai Publication No. 023/1998.

EXAMPLE 9

Into a wide mouthed bottle (140 ml) were placed 0.20 g of Y-form titanyl phthalocyanine described in Japanese Patent Kokoku Publication No. 35064/1991, 0.20 g of polyvinylbutyral resin [ELEX BH-3 manufactured by Sekisui Kagaku K.K.] and 59.6 g of cyclohexanone together with 50 g of 3 mm φ glass beads. After stirring by a paint shaker for 1 hour, the mixture was applied to an aluminum board, which had been washed carefully with acetone, using a bar coater to form a charge-generating layer (CGL) so that the thickness of film becomes 0.5 μm. Subsequently, onto the resulting charge-generating layer, a homogeneous solution, which had been prepared by mixing 4.5 g of the triarylamine dimer (α-NPD) prepared in Example 5, 4.5 g of a polycarbonate resin [PANLITE L-1250 manufactured by Teijin K.K.] and 51.0 g of chloroform and conducting ultrasonic dispersion, was applied with a bar coater to form a charge-transporting layer (CTL) so that the thickness of film becomes 60 μm. This was dried overnight to provide a photoreceptor (piece) for test.

EXAMPLE 10

A photoreceptor (piece) for test was prepared in the same manner as Example 9 except for replacing the Y-form titanyl phthalocyanine used in Example 9 with G-form μ-oxo-gallium phthalocyanine dimer (μ-oxo-Ga Pc dimer) described in Japanese Patent Kokai Publication No. 88023/1998.

Comparative Example 3

A photoreceptor (piece) for test was prepared in the same manner as Example 6 except for replacing the triarylamine dimer (synthesized in Example 1) with a butadiene-based charge-transporting agent (the chemical name: 1,1-bis(p-ethylaminophenyl)-1,3-butadiene; the trade name: T405; manufactured by Takasago Koryo K.K.) represented by the formula:

Evaluation of Photoreceptor Characteristics

As for the pieces of photoreceptor prepared in Examples 6 to 10 and Comparative Example 3, the primary photosensitive characteristics (OPC characteristics) were determined. Using an electrostatic paper analyzer model EPA-8200 [manufactured by Kawaguchi Denki K.K.], the piece was charged at −8.0 kV in the STAT 3 mode first, and after leaving in darkness for 2.0 seconds, it was exposed to white light of 5.0 lux for 10.0 seconds and determined its charged potential ($V_{max}$), dark decay ratio (%), residual potential ($V_{re}$) and half decay exposure amount (photoresponse) (E1/2). The measurements are summarized in Table 3.

TABLE 3

Evaluation results of primary photosensitive characteristics

| | CG material | CT material | $V_{max}$ (V) | Dark decay (%) | Vre (V) | E1/2 (1x · s) |
|---|---|---|---|---|---|---|
| Example 6 | Y-form Ti(=O) Pc | TPD (Example 1) | −365.3 | 32.2 | −25.7 | 0.60 |
| Example 7 | II-form μ-oxo-Al Pc dimer | TPD (Example 1) | −301.3 | 34.8 | −2.3 | 1.62 |
| Example 8 | G-form μ-oxo-Ga Pc dimer | TPD (Example 1) | −343.3 | 35.1 | −1.0 | 0.80 |
| Example 9 | Y-form Ti(=O) Pc | α-NPD (Example 5) | −259.0 | 36.1 | −2.7 | 0.68 |
| Example 10 | G-form μ-oxo-Ga Pc dimer | α-NPD (Example 5) | −242.3 | 41.2 | −2.3 | 0.97 |
| Comparative example 3 | Y-form Ti(=O) Pc | T-405 | −279.7 | 30.5 | −4.7 | 0.53 |

In the determination of dark decay ratio, the surface potential immediately after charging ($V_0=V_{max}$) and the surface potential 2.0-second after charging ($V_2$) were measured and the dark decay ratio (%) was determined according to the following equation:

Dark decay ratio (%)=100×($V_0-V_2$)/$V_0$

In the measurement of spectral photoresponse, the pieces of electrophotographic photoreceptor were charged ir the same manner as employed in the preceding evaluation of the photoreceptor characteristics except that the irradiation wavelength is changed in the range of from 450 to 900 nm at 50 nm (and 25 nm) intervals by using a band pass interference filter. The exposure energy was set to 1.00 $\mu$W. The initial charge ($V_{max}$ [V]) and the half decay exposure amount photoresponse (E1/2 [$\mu$J/cm$^2$]) were measured. The results were excellent.

In the durability test, the pieces of electrophotographic photoreceptor were charged in the same manner as employed in the preceding evaluation of the photoreceptor characteristics with setting the electrostatic paper analyzer model EPA-8200 to the durability measuring mode. In the durability measuring mode, the charging operation was repeated about 100 times. With repeating this operation, changes in the charged potential ($V_{max}$) and in the half decay exposure amount photoresponse (E1/2) were measured. The results were excellent.

EXAMPLE 11

In this example, an example of an organic film EL device using the TPD prepared in Example 1 as a hole-transporting material (HTM) is described.

A coating liquid was prepared by dissolving and dispersing tris(8-hydroxyquinoline) aluminum complex (a luminescent material), the TPD prepared in Example 1, a polycarbonate resin [PANLITE L-1250 manufactured by Teijin K.K.] in a ratio of 3:2:5 in chloroform. The coating liquid was coated on a washed glass board equipped with an ITO electrode by a spin coating method to form a 100 nm thick luminous layer. A 150 nm thick electrode made by alloy of magnesium and silver in a ratio of 10:1, was formed on the luminous layer to provide an organic EL device. When a direct-current power supply was connected to the device, and a direct current voltage of not less than 5 V was applied, green light was emitted from the device.

In the case of applying the TPD of the present invention to laminated EL devices (for example, anode/hole injecting layer/luminous layer/cathode), good emission luminance (cd/m$^2$) and good emission efficiency (lm/w) were observed.

EXAMPLE 12

In this example, an example of an organic film EL device using the α-NPD prepared in Example 5 as a hole-transporting material (HTM) is described.

A coating liquid was prepared by dissolving and dispersing tris(8-hydroxyquinoline) aluminum complex (a luminescent material), the α-NPD prepared in Example 5, a polycarbonate resin [PANLITE L-1250 manufactured by Teijin K.K.] in a ratio of 3:2:5 in chloroform. The coating liquid was coated on a washed glass board equipped with an ITO electrode by a spin coating method to form a 100 nm thick luminous layer. A 150 nm thick electrode made by alloy of magnesium and silver in a ratio of 10:1, was formed on the luminous layer to provide an organic EL device. When a direct-current power supply was connected to the device, and a direct current voltage of not less than 5 V was applied, green light was emitted from the device.

In the case of applying the α-NPD of the present invention to laminated EL devices (for example, anode/hole injecting layer/luminous layer/cathode), good emission luminance (cd/m$^2$) and good emission efficiency (lm/w) were observed.

According to the process of the present invention is provided a simple process for preparing triarylamine dimer (e.g., TPD or α-NPD) without using any expensive reagent. The process is able to achieve high reaction yield and is advantageous to be carried out on an industrial scale.

The TPD or α-NPD prepared by the process of the present invention can provide an organic electrophotographic photoreceptor having good OPC characteristics by its use in combination with a charge-generating material such as phthalocyanines when it is used as a charge-transporting material of an organic photoreceptor. Furthermore, when it is used as a hole-transporting material of an organic EL device, it can exhibit good emission luminance and good emission efficiency.

What is claimed is:

1. A process for preparing triarylamine dimer (I) sing the Ullmann reaction represented by the scheme:

wherein X represents a halogen atom, $R^1$ and $R^2$ represent independently a hydrogen atom, an alkyl group, an alkoxy group or a halogen atom, Ar represents a phenylene group, or a naphthylene group, characterized in that the reaction accelerator is polyethylene glycol or di- or monoalkyl ether of polyethylene glycol.

2. The process for preparing triarylamine dimer (I) according to claim 1, wherein X represents an iodine atom.

3. The process for preparing triarylamine dimer (I) according to claim 1, wherein $R^1$ represents a methyl group, $R^2$ represents a hydrogen atom, and Ar represents a phenylene group.

4. The process for preparing triarylamine dimer (I) according to claim 1, wherein $R^1$ and $R^2$ represent a hydrogen atom, and Ar represents an a-naphthylene group.

5. A process for preparing triarylamine dimer (I), comprising the step of undergoing the N-arylation reaction of 4,4'-dihalobiphenyl and diarylamine in the presence of base, a copper catalyst, and polyethylene glycol or di- or monoalkyl ether of polyethylene glycol as a reaction accelerator.

6. The process for preparing triarylamine dimer (I) according to claim 1 or 5, wherein the reaction accelerator is selected from the group consisting of the compounds represented by the following formulae (i) to (iii):

polyethylene glycol represented by the formula:

$$HO(CH_2CH_2O)_a\text{—}H \qquad (i)$$

wherein a represents an integer of not less than 2;

polyethylene glycol dialkyl ether represented by the formula:

$$R^3O(CH_2CH_2O)_b\text{—}R^4 \qquad (ii)$$

wherein $R^3$ and $R^4$ represent the same or different alkyl groups having 1 to 4 carbon atoms and b represents an integer of not less than 2;

polyethylene glycol monoalkyl ether represented by the formula:

$$R^3O(CH_2CH_2O)_c\text{—}H \qquad (iii)$$

wherein $R^3$ represents an alkyl group having 1 to 4 carbon atoms and c represents an integer of not less than 2.

* * * * *

UNITED STATES PATENT AND TRADEMARK OFFICE
CERTIFICATE OF CORRECTION

PATENT NO.   : 6,242,648 B1
DATED        : June 5, 2001
INVENTOR(S)  : Yasuhiro Yamasaki and Kazuyoshi Kuroda It is certified that error appears in the above-identified patent and that said Letters Patent is hereby corrected as shown below:

<u>Title page,</u>
Item [30], change "August 1, 1999" to -- January 8, 1999 --

Signed and Sealed this

Thirty-first Day of December, 2002

JAMES E. ROGAN
*Director of the United States Patent and Trademark Office*